United States Patent
Estoque et al.

(10) Patent No.: US 6,343,177 B1
(45) Date of Patent: Jan. 29, 2002

(54) OVER-MOLDED REFLECTIVE OPTICAL FIBER TERMINAL

(75) Inventors: Daniel A. Estoque; Kevin A. Keilbach, both of Boulder, CO (US)

(73) Assignee: Datex-Ohmeda, Inc., Louisville, CO (US)

(*) Notice: Subject to any disclaimer, the term of this patent is extended or adjusted under 35 U.S.C. 154(b) by 0 days.

(21) Appl. No.: 09/277,852

(22) Filed: Mar. 26, 1999

(51) Int. Cl.$^7$ ................................. G02B 6/00
(52) U.S. Cl. ..................... 385/139; 385/73; 385/74; 385/76
(58) Field of Search ................ 385/134, 73, 76, 385/74

(56) References Cited

U.S. PATENT DOCUMENTS

| | | | |
|---|---|---|---|
| 3,806,225 A | 4/1974 | Codrino | 350/96 B |
| 4,021,099 A | 5/1977 | Kawasaki et al. | 350/96 C |
| 5,125,054 A | * 6/1992 | Ackley et al. | 385/49 |
| 5,337,377 A | 8/1994 | Yamada et al. | 385/15 |
| 5,408,558 A | * 4/1995 | Tan | 385/80 |
| 5,640,262 A | 6/1997 | Hanai et al. | 359/195 |
| 5,793,916 A | * 8/1998 | Dahringer et al. | 385/95 |

FOREIGN PATENT DOCUMENTS

EP  0 781 527 A1  11/1996  ............ A61B/5/00

* cited by examiner

Primary Examiner—Frank G. Font
Assistant Examiner—Reginald A. Ratliff
(74) Attorney, Agent, or Firm—Marsh, Fischmann & Breyfogle LLP

(57) ABSTRACT

An over molded reflective optical fiber terminal (100) generally includes an end portion of an optical fiber (102) that has been stripped of its buffer (104), a terminal block (106), an integral mirror (108) formed on the terminal block (106), and an optical element such as a window (112). The terminal block (106) is preferably formed from transparent injection molded plastic. The block can be molded so as to define a profile for the mirror (108). By virtue of this design, construction and alignment of the terminal/mirror system is simplified and costs are reduced. In addition, the reflective surface of the mirror (108) may be protected against dust or other optical interference. Moreover, a compact reliable terminal system for off axis application is provided.

23 Claims, 3 Drawing Sheets

OVER-MOLDED REFLECTIVE OPTICAL FIBER TERMINAL

FIELD OF THE INVENTION

The present invention relates in general to terminals for optical fibers and, in particular, to an over-molded terminal with an integral reflector for non-axial signal communication applications. The invention has particular advantages for certain photoplethysmography applications.

BACKGROUND OF THE INVENTION

Optical fibers are used to transmit optical signals in a variety of applications including communications, spot or area illumination and photoplethysmography, e.g., pulse oximetry. The associated optical systems typically include one or more fiber terminals where signals are transmitted to and/or from an end of an optical fiber. In this regard, such terminals are often associated with optics such as lenses or mirrors, for example, for focusing an incoming signal onto the fiber end, for forming an outgoing signal into a beam, for diffusing an outgoing signal as may be desired or for various other functions. One important function of such optics is to receive or transmit non-axial signals, i.e., signals not aligned with the optical axis extending from the fiber end. It may be desired to transmit or receive non-axial signals, for example, in order to reduce optical system dimensions, to couple the optical fiber with other optical components that are constrained to being located off-axis, or to facilitate selective coupling of the fiber relative to multiple optical devices which cannot all be disposed on-axis.

Accordingly, it is often desired to provide a reflector or mirror in connection with a fiber terminal. Depending on the intended use of the mirror, many different optical, construction and maintenance issues may need to be considered in connection with the terminal/mirror interface. One of these issues relates to the relative positioning of the fiber end and the mirror. The fiber end generally must be securely anchored and the mirror must be carefully positioned on the fiber axis in order to allow for proper optical coupling of the mirror to the optical fiber. The angular orientation of the mirror generally must also be controlled in relation to the overall optical system for proper alignment so as to reduce optical losses. Additionally, the distance between the fiber end and the mirror may need to be selected in conjunction with the mirror shape such that incoming signals are focused or contrasted on the fiber end, or outgoing signals from the fiber end are focused, collimated or diffused as desired, etc. Moreover, for maintenance purposes, the mirror may need to be sealed or be accessible for cleaning in order to maintain acceptable optical performance. It will thus be appreciated that the design, construction and maintenance of fiber terminals and associated optics can be complicated and expensive.

SUMMARY OF THE INVENTION

The present invention is directed to an integrated fiber terminal and reflector system for use in a variety of off-axis signal transmission applications including transmitting and/or receiving signals that are off-axis relative to a terminated fiber. The invention substantially simplifies construction, alignment and maintenance, and allows for reduced production costs as well as improved optical performance. As set forth below, the invention has particular advantages for certain photoplethysmography applications such as pulse oximetry due to its compactness of design, ease of construction and alignment, and low production costs for probes that may be disposed of after a single use or few uses.

According to one aspect of the present invention, a reflective surface is integrally formed on a signal transmissive terminal structure in which a fiber is anchored. The corresponding terminal includes a terminal structure for fixedly retaining an end portion of the optical fiber such that the fiber end portion defines a fiber axis extending axially from the end portion, and a reflective surface integrally formed on the terminal structure and extending across the fiber axis. The terminal structure includes an optically transmissive portion extending across the fiber axis. Preferably, the optically transmissive material is substantially transparent to at least one wavelength of interest. For example, the terminal structure or a portion thereof may be formed from transparent plastic that is molded over the end portion of the fiber. The reflective surface is operative for reflecting signals relative to the fiber axis and a reflection axis, i.e., reflecting signals from the fiber axis to the reflection axis or vice versa. Preferably, the reflective surface is integrally formed on the terminal structure by applying a reflective film or other reflective material to an external surface of the terminal structure. In this regard, the exterior surface of the terminal structure may be shaped to impart the desired optical properties to the reflective surface, e.g., concentrating/focusing, collimating, or diffusing optical signals incident thereon. By virtue of the present invention, construction and alignment of the terminal/mirror system is simplified and costs are reduced. In addition, the reflective surface may be protected against dust or other optical interference. Moreover, a compact and reliable terminal system for off-axis applications is provided.

If desired, a further optical device may be mounted on the terminal structure. For example, the optical device may be mounted on an exterior surface of the terminal structure extending across the reflection axis in order to operate on signals transmitted along the reflection axis, e.g., incoming or outgoing signals. Depending on the application, the optical device may perform any of various functions. For example, the optical device may diffuse signals transmitted from the optical fiber in order to illuminate a desired area. Alternatively, the optical device may collimate, concentrate or focus signals transmitted from the optical fiber onto a further optical element such as another optical fiber, a lens, or an optical detector. Conversely, the optical device may operate on incoming signals, for example, to focus or assist in focusing the incoming signal onto the end of the terminated optical fiber.

According to another aspect of the present invention, a method is provided for forming an optical fiber terminal. The method includes the steps of providing an optical fiber having an exterior buffer material, removing the buffer material from an end portion of the fiber, molding an optically transmissive material over the end portion of the fiber, and applying a reflective material to an exterior surface of the molded, optically transmissive material such that the reflective material extends across an axis of the fiber. The buffer material may be a liner material such as is commonly provided in connection with optical fibers to prevent accidental breakage or shield ambient light. Such buffer material can be removed from the end portion by way of a conventional stripping operation. The optically transmissive material may then be molded over the end portion of the fiber, for example, by way of injection molding transparent plastic on the optical fiber end. As part of this molding process, and exterior surface of the plastic may be shaped to impart desired optical properties to the reflective material subsequently applied to the exterior surface. Depending on the nature of the optically transmissive material and the reflective material, the reflective material may be applied by direct deposition onto the optically transmissive material adhesive bonding, or other processes. In the case of adhesive bonding, the adhesive may be applied outside of the area of the reflective surface or an index matched adhesive may be employed. In all such cases, it is an advantage of the present invention that the reflective material is integrally formed on the terminal structure such that proper optical performance is insured.

In one embodiment, the optical terminal of the present invention is implemented in connection with a pulse oximeter probe. Pulse oximetry generally involves transmission of optical signals of a predetermined wavelength or wavelengths through a portion of a patient's body such as a finger, ear lobe or the like. The optical signal transmitted through the patient's tissue is then detected and can be analyzed to determine oxygen saturation, perfusion or the like as is well known. It is desirable to provide the portion of the oximeter instrument which engages the patient in the form of a detachable probe. Such a probe may be disposed of after a single use or a small number of uses. Accordingly, it is desirable to reduce the cost of the probe by locating relatively few components in the probe but, rather, locating most of the active and expensive components in an oximeter housing to which the probe is coupled. Thus, for example, the use of fiber optics can allow a signal source and/or a signal detector to be located in the housing.

Accordingly, the probe may include a transmitting fiber and associated optics and/or receiving fiber and associated optics. Alternatively, the receiving fiber and associated optics may be replaced by a detector and electrical leads. The probe also includes a housing structure for engaging the patient. For example, the housing may be shaped and dimensioned for engaging a patient's finger. In accordance with the present invention, the terminal of the present invention may be engaged within the probe housing structure for transmitting and/or receiving pulse oximetry signals. In this regard, the terminal structure may be bonded to the probe housing structure or may be removably inserted into the housing structure with appropriate mechanisms to insure proper registration of the transmitting and receiving elements.

BRIEF DESCRIPTION OF THE DRAWINGS

For a more complete understanding of the present invention and further advantages thereof, reference is now made to the following detailed description taken in conjunction with the drawings in which.

DETAILED DESCRIPTION

In the following description, the invention is set forth in the context of a specific overmolded reflective optical fiber terminal and embodiments where the terminal is incorporated into a pulse oximetry housing. It should be appreciated however that various aspects of the invention may be implemented in other types of fiber terminals and in other applications.

Figure 1:
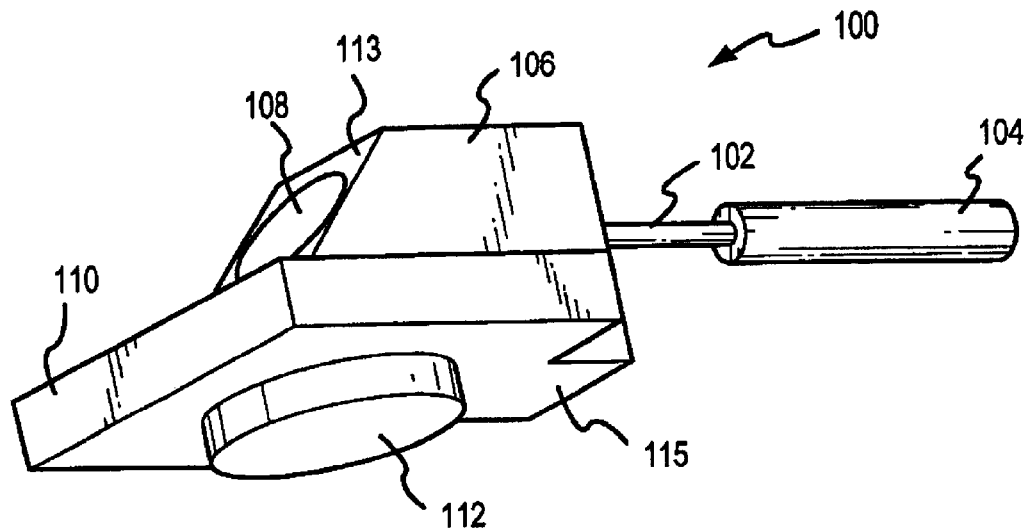
FIG. 1 is a perspective view showing a fiber optic terminal in accordance with the present invention.
Figure 2:
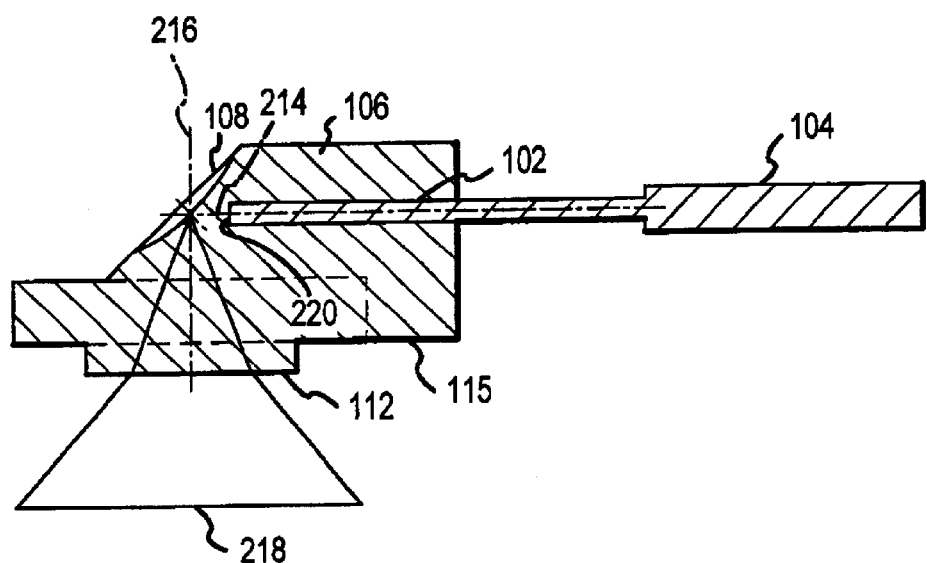
FIG. 2 is a side cross sectional view of the terminal of FIG. 1.
Figure 3:
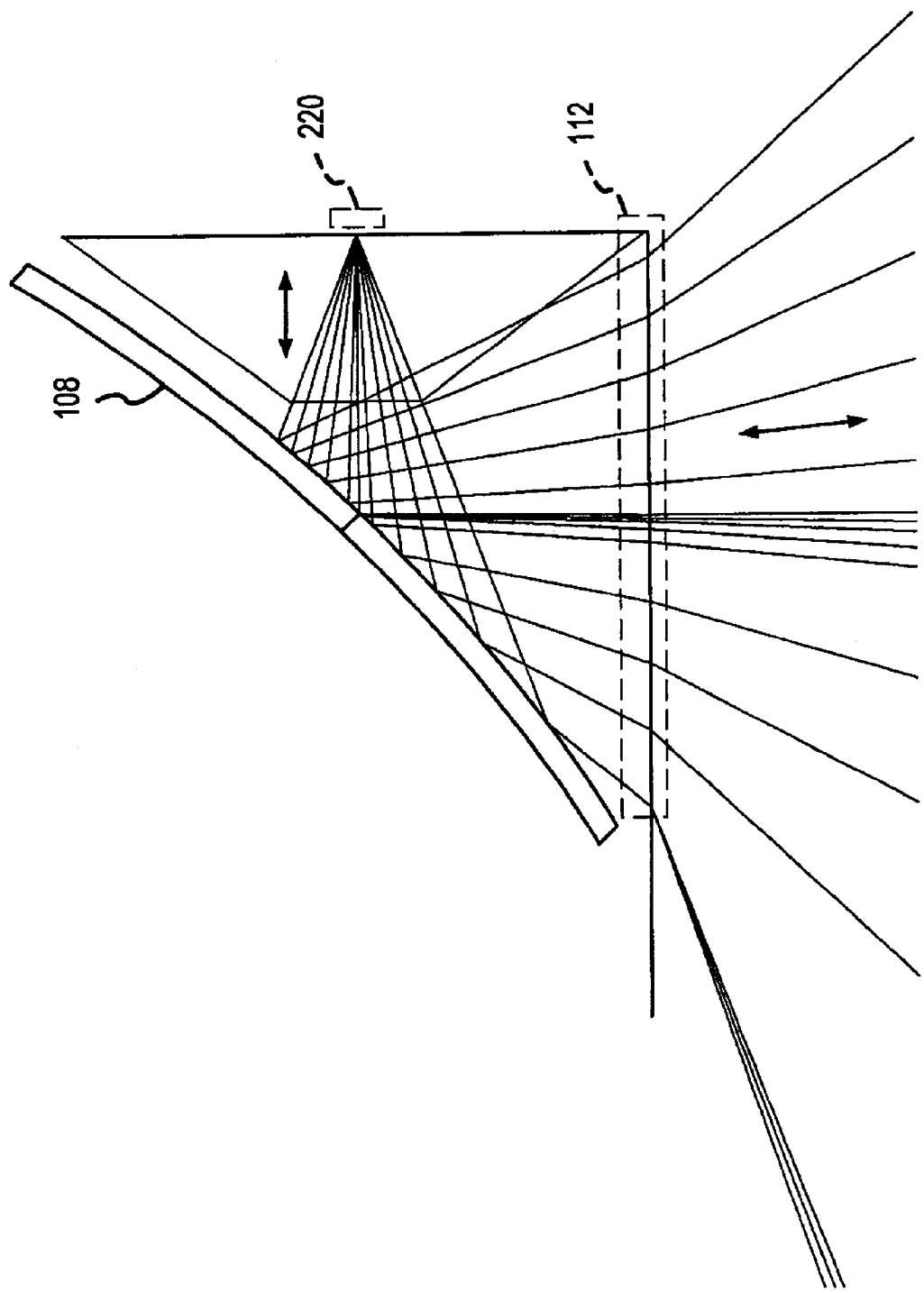
FIG. 3 is a ray diagram illustrating the optical performance of the terminal of FIG. 1.

Referring to FIGS. 1–3, an overmolded reflective optical fiber terminal is generally identified by the reference numeral 100. The terminal 100 generally includes an end portion of an optical fiber 102 that has been stripped of its buffer 104, a terminal block 106, an integral mirror 108 formed on the terminal block 106, and an optical element such as a window 112. Each of these components will be described in turn below.

The optical fiber 102 may be any of various optical fibers that are known or may hereafter be developed. Typically, such optical fibers include an optical fiber core surrounded by coaxial cladding. The cladding generally operates to reflect radiation at the core/cladding interface so that optical signals can be transmitted through the core with minimal optical losses. The illustrated fiber also includes a coaxial buffer 104 surrounding the fiber. Such buffer materials are typically provided to strengthen the optical fiber so as to avoid accidental breakage. In addition, the buffer may further insulate the fiber core from ambient light which could increase noise levels. For the purposes of pulse oximetry applications such as discussed below, the optical fiber 102 is preferably suitable for transmitting near infrared optical signals. As shown, the fiber 102 is stripped of the buffer 104 at an end portion thereof where the fiber extends into the terminal block 106.

The illustrated terminal block performs a number of functions. First, the terminal block anchors the fiber end 220 of fiber 102. In this regard, it will be appreciated that, for certain applications, it is important to fix the position of the fiber end relative to the mirror 108 and other optical components of an optical system. For example, if the fiber 102 is intended to receive optical signals via the window 112 and mirror 108, it may be important for the fiber end 220 to be located in a focal plane of the mirror 108 or otherwise positioned such that incoming signals are concentrated on the fiber end 220. Relatedly, it may be important for the relative positioning of the fiber end 220 and mirror 108 to be maintained such that the mirror 108 is located on the fiber axis 214 whereby the fiber axis 214 is coupled with reflection axis 216 via the mirror 108. Such relative positioning can be controlled by appropriately forming the terminal block 106.

The terminal block 106 also supports the mirror 108 and window 112. As will be described in more detail below, external surface 113 of terminal block 106 may be formed to impart the desired optical qualities to the mirror 108. For example, external surface 113 may have a convex profile so as to concentrate or focus an incoming beam transmitted through window 112 onto the fiber end 220. Alternatively, as shown, the mirror 108 may have a concave profile so as to diffuse the signal transmitted from fiber 102. In the illustrated embodiment, it will be appreciated that the concave mirror 108 is also reversibly operative for concentrating an incoming signal onto the fiber end 220 as generally shown in the ray diagram of FIG. 3. External surface 105 may be used for mounting an optical component such as window 112. Thus, the position, shape and angular orientation of the external surface can be selected in relation to the window 112, mirror 108, and fiber end 220 so as to provide the desired optical performance.

The illustrated terminal block 106 also includes a flange 110. As shown, the flange 110 provides a widened mounting surface 115 for window 112. The flange 110 may also be useful, as described below, for mating with complementary structure of a pulse oximetry probe housing (or other structure for other applications), so as to insure proper registration of the terminal 100 with other optical components.

The mirror 108 couples the fiber axis 214 with the reflection axis 216. Accordingly, the mirror may operate to reflect signals transmitted from the fiber 102 onto the reflection axis 216 and/or reflect incoming signals from reflection axis 216 into the fiber 102 via fiber axis 214. As noted above, external surface 113 may be formed to define the mirror 108. The mirror 108 can then be completed by applying a reflective material onto the formed surface 113. The reflective material may be applied in various ways depending on the nature of the terminal block and the reflective material. For example, if the terminal block was formed from glass, the reflective material may be directly deposited onto the terminal block 106 such as via sputtering. In the illustrated embodiment, the terminal block 106 is formed of injection molded plastic and the reflective material is bonded thereto. In this regard, the reflective material may be applied by spraying, by providing a separate film that is adhered to the terminal block 106 via heating, or via an adhesive applied across or outside of the reflective surface. Where the adhesive is applied across the reflective surface, a transparent, index matched adhesive is preferably employed. Regarding optical performance, the reflective material is preferably highly reflective at least with regard to the wavelengths of interest. In the illustrated embodiment, the reflective material is a spray coating of infrared reflective film.

Various types of optical components may be mounted on surface 115. For example, a collimating lens may be employed to form an output collimated beam and/or to concentrate an incoming beam on the fiber end in conjunction with the mirror 108. Alternatively, a concentrating or focusing lens may be employed, for example, to focus a transmitted signal onto a detector surface or the end of an optically coupled fiber or optics associated with a coupled fiber. In the illustrated embodiment, a diffusive window 112 is mounted on surface 115. Such a diffusive window may be desirable in connection with various applications such as pulse oximetry, in order to provide a broadened beam 218. In pulse oximetry, such a broadened beam may be preferable to reduce errors resulting from bone, veins or other artifact. Optionally, an optical band pass filter may be implemented in conjunction with the window 112 to minimize the admittance of ambient light or other optical noise.

The illustrated terminal 100 can be formed as follows. First, a fiber 102 is obtained and the buffer 104 is stripped from an end portion of the fiber 102 in conventional fashion. The terminal block 106 can then be injection molded onto the fiber end 220 by inserting the fiber end 220 into a mold and injecting transparent plastic so as to form the terminal block 106. The mirror 108 can then be completed by spray coating reflective material onto surface 113 or otherwise applying a reflective film to the surface 113 such as via heating or an adhesive. The window 112 or other optics can then be applied to surface 115 using an adhesive such as an index matched transparent adhesive applied between the window 112 and the surface 115. The placement of the mirror 108 is controlled by the design of the mold. Similarly, the placement of the window 112 can be controlled by molding an appropriate indentation into surface 115. Alternatively, placement of the window 112 may be selected by transmitting an optical signal through the fiber 102 and then moving the window 112 until the desired output effect is achieved.

Figure 4:
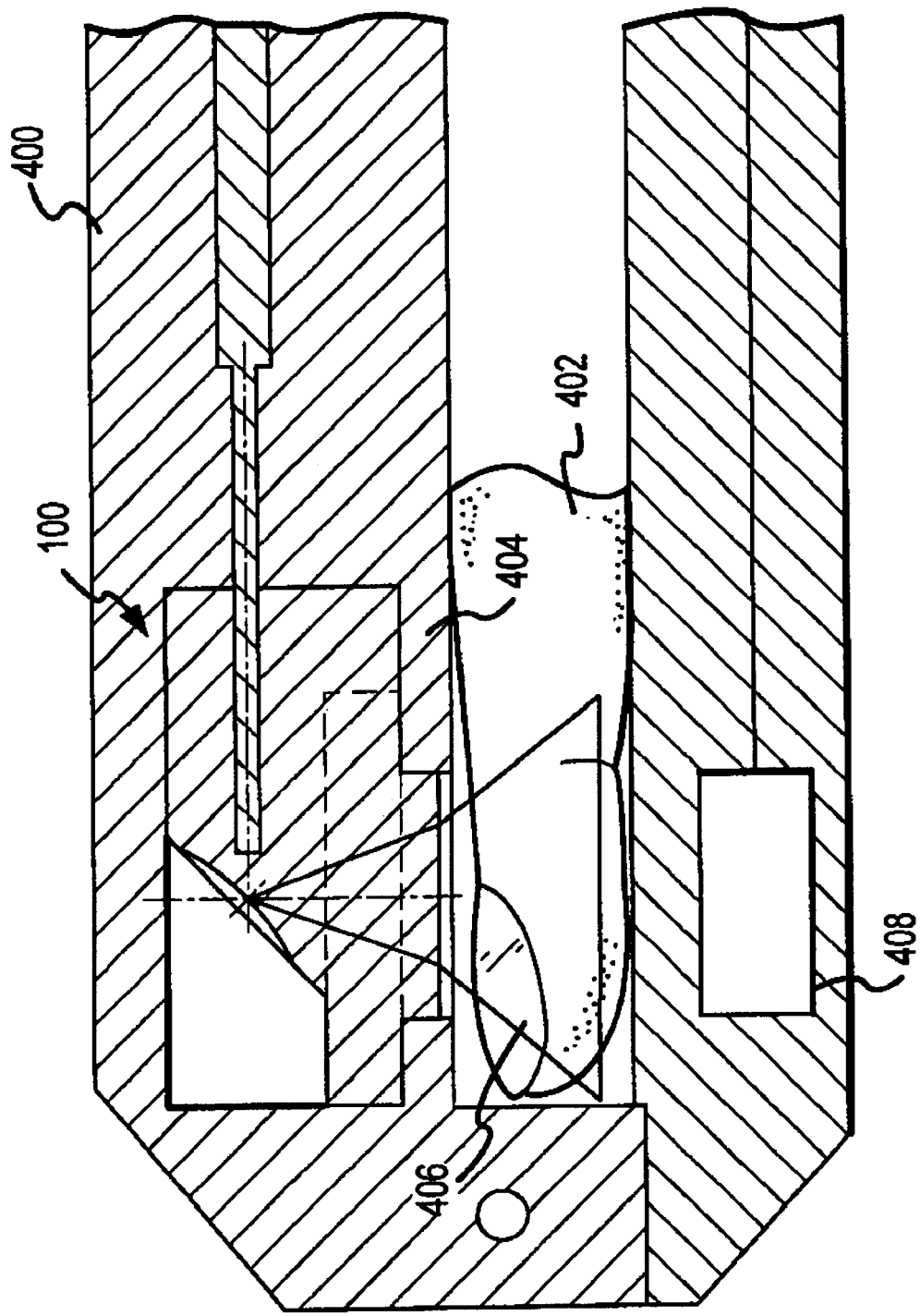
FIG. 4 is a side cross sectional view, partially schematic, showing the terminal of FIG. 1 incorporated into a pulse oximetry housing.

FIG. 4 shows a side cross sectional view, partially schematic, of a pulse oximetry housing 400 incorporating the terminal 100. As is well known, pulse oximetry relates to transmitting optical signals through tissue in order to determine oxygen saturation, perfusion or the like. Generally, the transmitted optical signal includes one or more wavelengths where oxygen related analytes of interest have an absorption peak or other spectral characteristic that can be quantified. Accordingly, pulse oximetry generally involves transmitting a radiation signal through tissue and detecting the radiation signal transmitted through the tissue. In the illustrated embodiment, the probe housing 400 is of a type commonly used to engage a patient's finger 402 and is generally shaped and dimensioned to extend over the end of the patients finger. A spring or the like is typically provided in conjunction with the housing so that the housing securely clamps onto the patient's finger. The illustrated terminal 100 is used to transmit an optical signal 406 through the finger 402. The transmitted signal is then received by a detector element 408 on the opposite side of the patient's finger 402. Although only shown schematically, it will be appreciated that the detector element 408 may include detectors such as photo diodes that are located in the probe housing 400. Alternatively, the detector element 408 may include a further fiber optic terminal for capturing the transmitted signal and transmitting the signal via an optical fiber to a detector unit located in a remote housing.

In the illustrated embodiment, the terminal 100 is located within a complementary shaped portion 404 of the probe housing 400. Such complementary shaping holds the terminal 100 securely in place and assures proper registration relative to the detector structure 408. In this regard, the probe housing 400 may be hinged to allow insertion of the terminal. Alternative designs may allow the terminal 100 to be engaged within the housing 400 by way of adaptors that engage with a snapping action. Additionally, although not shown, the terminal 100 may be secured in place using an adhesive if desired.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An optical fiber terminal, comprising:

A terminal structure for fixedly retaining an end portion of an optical fiber, wherein said end portion defines a fiber axis extending axially from said end portion of said fiber, said terminal structure including an optically transmissive portion extending across said fiber axis; and a reflective surface integrally formed on said terminal structure and extending across said optical axis and a reflection axis so as to reflect signals relative to said fiber axis and said reflection axis;

wherein said reflective surface is operative for one or more of reflecting a signal transmitted along said reflection axis to said end portion of said fiber via said fiber axis and reflecting a signal transmitted from said end portion of said fiber along said fiber axis to said reflection axis.

2. An optical fiber terminal as set forth in claim 1, wherein said terminal structure comprises a substantially optically transparent material extending on said optical path from said end portion of said fiber to said reflective surface.

3. An optical fiber terminal as set forth in claim 1, wherein said terminal structure comprises optically transmissive plastic molded over said end portion of said fiber.

4. An optical fiber terminal as set forth in claim 1, wherein said reflective surface is disposed on an exterior surface of said terminal structure.

5. An optical fiber terminal as set forth in claim 1, wherein said reflective surface comprises a reflective film applied to an external surface of said terminal structure.

6. An optical fiber terminal as set forth in claim 1, wherein a shape of said reflective surface is defined by a molded exterior surface of said terminal structure.

7. An optical fiber terminal as set forth in claim 1, wherein said terminal structure includes a window disposed on said reflection axis.

8. An optical fiber terminal as set forth in claim 7, wherein said reflective surface is shaped so as to optically form a signal transmitted along one of said fiber axis and said reflection axis.

9. An optical fiber terminal as set forth in claim 7, wherein said window is operative to optically form a signal transmitted along said reflection axis.

10. An optical fiber terminal as set forth in claim 1, wherein said reflective surface is shaped and positioned to concentrate an optical signal transmitted along said reflection axis into said end portion of said fiber.

11. An optical fiber terminal as set forth in claim 1, wherein said reflective surface is shaped and positioned so as to diffuse an optical signal transmitted from said end portion of said fiber.

12. An optical fiber terminal as set forth in claim 1, wherein said reflective surface is shaped and positioned so as to allow an optical signal transmitted from said end portion of said fiber to be focused at a desired plane.

13. An optical fiber terminal as set forth in claim 1, further comprising means for mounting said terminal structure in an oximeter housing.

14. An optical fiber terminal, comprising:

an optically transmissive material molded over an end portion of an optical fiber such that said end portion is anchored therein, said anchored fiber end thereby defining a fiber axis extending axially from said end portion of said fiber through said optically transmissive material;

an exterior surface of said optically transmissive material extending across said fiber axis; and a reflective material disposed on said exterior surface and extending across said fiber axis.

15. An optical fiber terminal as set forth in claim 14, wherein said optically transmissive material comprises injection molded plastic.

16. An optical fiber terminal as set forth in claim 14, wherein said reflective material is disposed at an angle relative to said fiber axis so as to optically connect said fiber axis to a reflection axis.

17. An optical fiber terminal as set forth in claim 16, further comprising an optical device mounted on said optically transmissive material and extending across said reflection axis.

18. An optical fiber terminal as set forth in claim 14, further comprising means for mounting said optically transmissive material in an oximeter housing.

19. A method for use in forming an optical fiber terminal, comprising the steps of:

providing an optical fiber having an exterior buffer material;

removing said buffer material from an end portion of said fiber;

molding an optically transmissive material over the end portion of the fiber, wherein an exterior surface of the molded, optically transmissive material extends across a fiber axis extending axially from the end portion of the fiber; and applying a reflective material to the exterior surface of the molded, optically transmissive material such that said reflective material extends across the fiber axis.

20. A method as set forth in claim 19, wherein said step of molding comprises forming said exterior surface at an angle relative to said fiber axis such that said reflective material optically connects said fiber axis to a reflection axis transverse thereto.

21. A method as set forth in claim 20, wherein said step of molding comprises shaping said exterior surface such that said reflective material optically forms in a predetermined manner a signal transmitted along one of said fiber axis and said reflection axis.

22. A method as set forth in claim 20, further comprising the step of mounting an optical device on said optically transmissive material extending across said reflection axis.

23. A method as set forth in claim 19, further comprising the step of mounting said optically transmissive material in an oximeter housing.

\* \* \* \* \*